United States Patent [19]

Pattillo et al.

[11] Patent Number: 4,937,194

[45] Date of Patent: Jun. 26, 1990

[54] METHOD FOR METERING NUTRIENT MEDIA TO CELL CULTURE CONTAINERS

[75] Inventors: Martha C. Pattillo, Evanston; David V. Bacehowski, Wildwood; Arnold C. Bilstad, Deerfield, all of Ill.; Herbert M. Cullis, Silver Spring, Md.; T. Michael Dennehey, Arlington Heights, Ill.; James W. Yang, Schaumburg, Ill.; William C. Brown, Palatine, Ill.

[73] Assignee: Baxter International Inc., Deerfield, Ill.

[21] Appl. No.: 303,188

[22] Filed: Jan. 30, 1989

Related U.S. Application Data

[62] Division of Ser. No. 862,344, May 12, 1986, Pat. No. 4,829,002.

[51] Int. Cl.$^5$ ............................ C12N 5/00; B65B 3/00
[52] U.S. Cl. ........................... 435/240.2; 435/240.241; 435/240.25; 435/240.26; 435/800; 141/10
[58] Field of Search ................ 435/2, 240.2, 240.21, 435/240.23, 240.24, 240.241, 240.242, 240.25, 240.26, 240.3, 284–286, 299–301, 313, 800; 604/407–410; 141/10

[56] References Cited

U.S. PATENT DOCUMENTS

| | | | |
|---|---|---|---|
| Re. 31,135 | 2/1983 | Winchell et al. | 222/107 |
| Re. 32,056 | 12/1985 | Granzow et al. | 141/1 |
| 667,947 | 2/1901 | Morrison | 141/244 X |
| 3,027,305 | 3/1962 | Freeman | 435/310 X |
| 3,084,606 | 4/1978 | Mittleman | 137/102 |
| 3,102,082 | 8/1963 | Brewer | 435/30 |
| 3,184,395 | 5/1965 | Brewer | 435/813 |
| 3,223,595 | 12/1965 | Brewer | 435/299 |
| 3,566,930 | 3/1971 | Kirschner | 141/244 |
| 3,650,093 | 3/1972 | Rosenberg | 604/152 X |
| 3,698,450 | 10/1972 | Taylor et al. | 141/85 |
| 3,749,646 | 7/1973 | Pirt | 435/254 |
| 3,821,087 | 6/1974 | Knazek et al. | 435/285 |
| 3,870,602 | 3/1975 | Froman et al. | 435/299 X |
| 3,926,723 | 12/1975 | Green et al. | 435/240.3 |
| 3,941,662 | 3/1976 | Munder et al. | 435/284 |
| 3,952,729 | 4/1976 | Libman et al. | 128/762 |
| 4,033,825 | 7/1977 | Haddad et al. | 435/284 |
| 4,036,698 | 7/1977 | Bush et al. | 435/31 |
| 4,040,909 | 8/1977 | Libman et al. | 435/292 |
| 4,105,500 | 8/1978 | Libman et al. | 435/30 |
| 4,140,162 | 2/1979 | Gajewski et al. | 428/35 |
| 4,142,940 | 3/1979 | Modolell et al. | 435/313 |
| 4,166,768 | 9/1979 | Tolbert et al. | 435/286 |
| 4,178,209 | 12/1979 | Tolbert et al. | 435/240.24 |
| 4,184,916 | 1/1980 | Tolbert et al. | 435/240.25 |
| 4,201,845 | 5/1980 | Feder et al. | 435/285 |
| 4,253,501 | 3/1981 | Ogle | 604/407 |
| 4,332,247 | 6/1982 | Mittleman et al. | 604/82 |
| 4,336,329 | 6/1982 | Hesse et al. | 435/3 |
| 4,346,703 | 8/1982 | Dennehey et al. | 604/406 |
| 4,351,900 | 9/1982 | Lemonnier | 435/31 |
| 4,376,822 | 3/1983 | Braude | 435/240.25 |

(List continued on next page.)

*Primary Examiner*—Christine M. Nucker
*Assistant Examiner*—William H. Beisner
*Attorney, Agent, or Firm*—Bradford R. L. Price; Paul C. Flattery; Garrettson Ellis

[57] ABSTRACT

A system for metering nutrient media to cell culture containers includes a media flow conduit which defines at one end means for substantially aseptic communication with the source of the media. In a preferred embodiment, sterile connectors may be used for essentially sterile conditions. A branch conduit extends from the flow conduit at a location spaced from the ends. The branch conduit communicates with means for receiving a predetermined-volume aliquot of media through the media flow conduit from said one end. The flow conduit also defines a portion downstream from the branch conduit, which communicates with at least one cell culture container, each container being a flexible bag. At least part of the flexible bag is made of a material capable of providing at least 2 times the oxygen diffusion and at least 2 times the carbon dioxide diffusion between the bag interior and exterior, compared with an identically-sized, sealed bag having polyethylene walls 0.013 inch thick.

8 Claims, 5 Drawing Sheets

U.S. PATENT DOCUMENTS

| | | | |
|---|---|---|---|
| 4,391,912 | 7/1983 | Yoshida et al. | 435/240.25 |
| 4,397,945 | 8/1983 | Lemonnier | 435/31 |
| 4,433,974 | 2/1984 | Bischof | 604/407 |
| 4,452,473 | 6/1984 | Ruschke | 604/905 |
| 4,514,499 | 4/1985 | Noll | 435/240 |
| 4,517,293 | 5/1985 | Fabricius et al. | 435/68 |
| 4,546,083 | 10/1985 | Meyers et al. | 435/240 |
| 4,629,686 | 12/1986 | Gruenberg | 435/1 |
| 4,650,766 | 3/1987 | Harm et al. | 435/284 |
| 4,673,399 | 6/1987 | Pruett | 604/272 |
| 4,690,915 | 9/1987 | Rosenberg | 514/2 |
| 4,749,654 | 6/1988 | Karrer et al. | 435/240.25 |

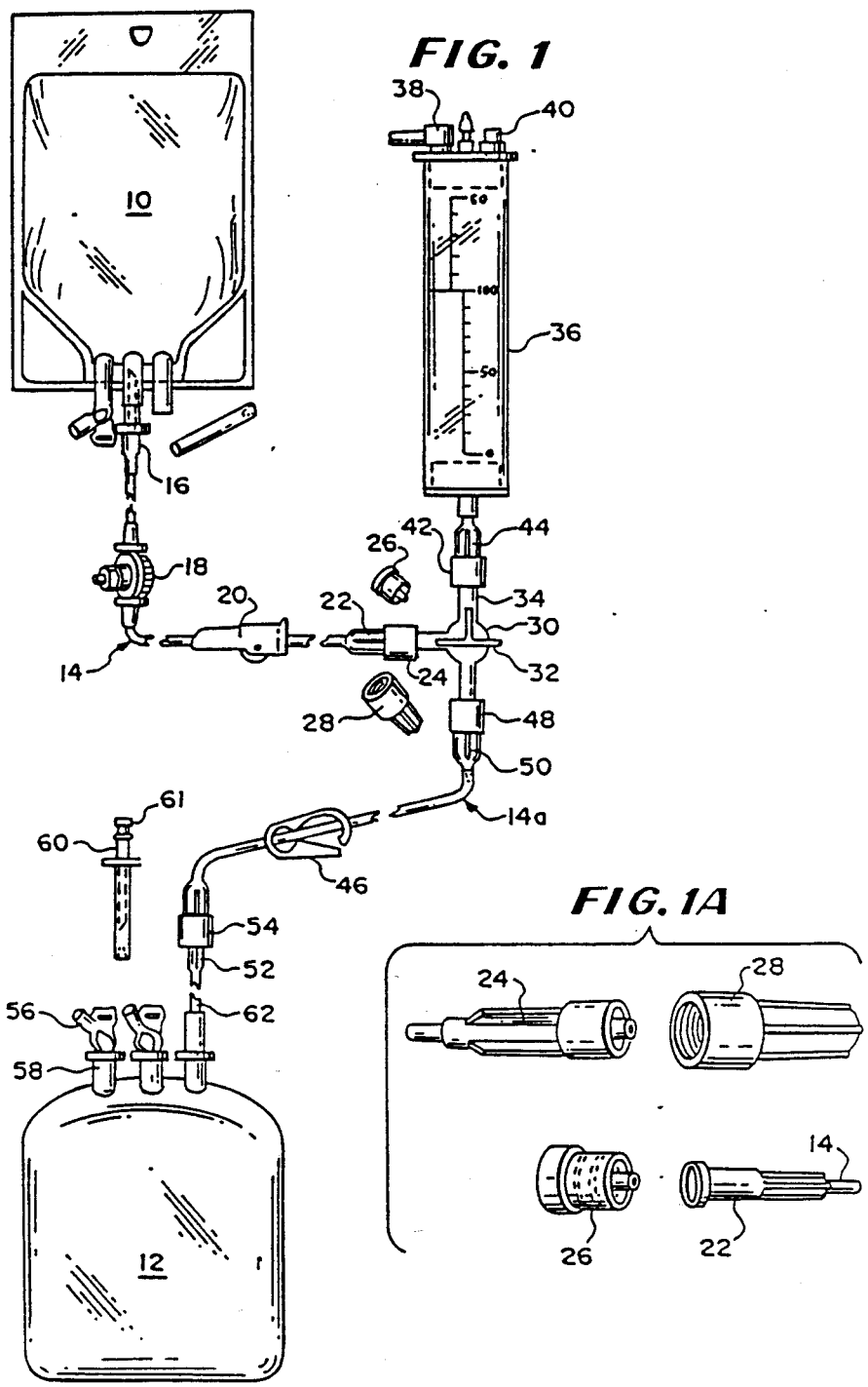

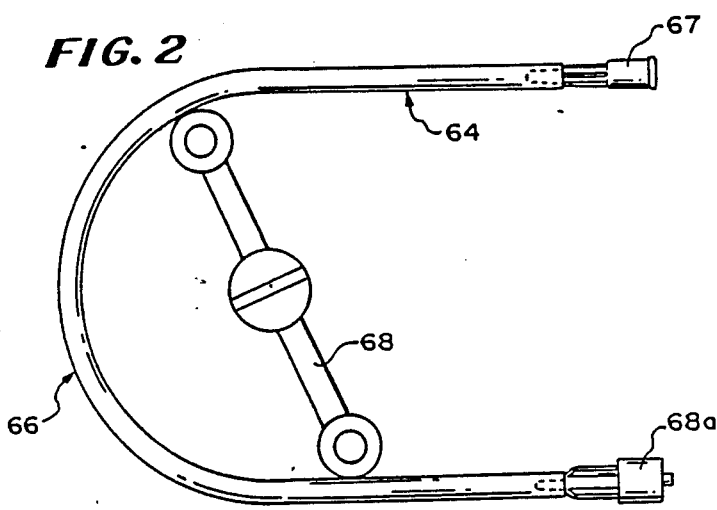
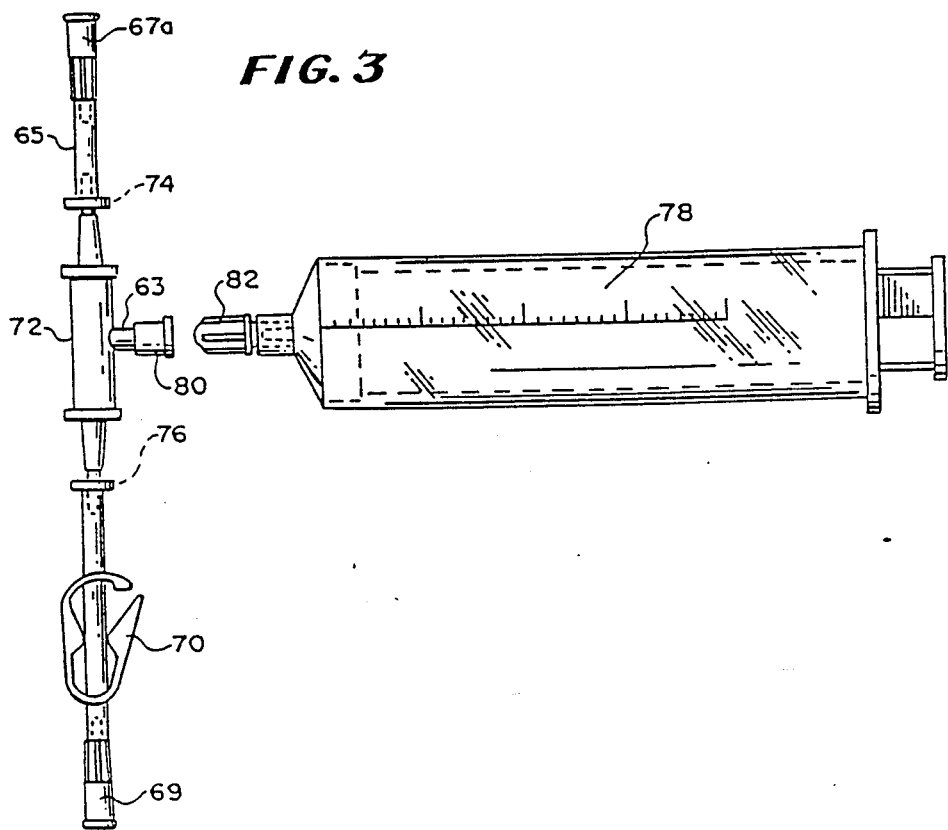

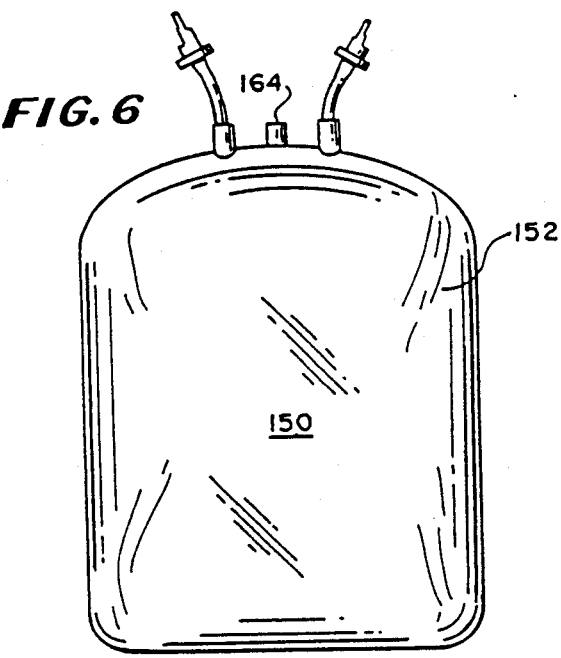
FIG. 6
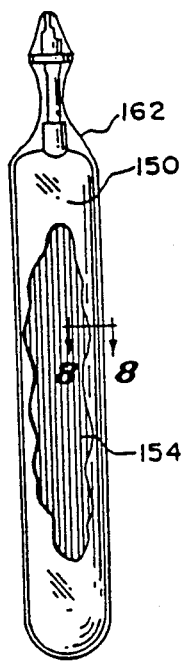
FIG. 7
FIG. 8
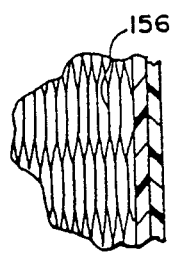
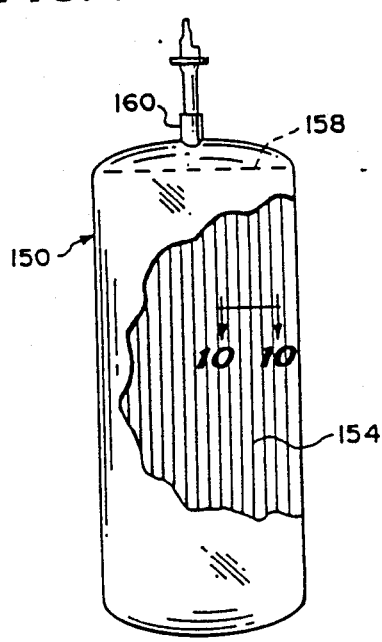
FIG. 9
FIG. 10
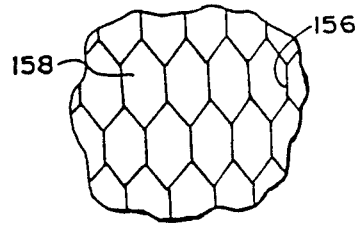

METHOD FOR METERING NUTRIENT MEDIA TO CELL CULTURE CONTAINERS

This is a division of application Ser. No. 862,344, filed May 12, 1986, now U.S. Pat. No. 4,829,002.

In the culturing of cells, for example hybridoma cells for manufacturing monoclonal antibodies or the like, the typical cell container is a roller bottle which is placed in a machine to gently agitate the contents during cell culturing operation. The systems of the prior art are fairly labor intensive and wasteful of space. Also, prior art systems may be "open" systems, in that their interiors must be opened at some time during use, creating the possibility of bacterial contamination. Thus, a laminar flow hood may be needed to use the systems.

Spinner flasks with paddles, and stationary flasks in incubators, are also used to culture cells. However, such systems are also open systems. Likewise, all of the above systems are quite labor intensive in their use, thus being expensive, inconvenient, and unreliable for maintaining aseptic conditions.

In many current culturing techniques the cap of the flask must be left partly open for gas exchange in a conventional incubator, with a resulting risk of contamination by unwanted microorganisms.

It has been suggested in the patent literature and elsewhere to use bags made of gas permeable plastic to culture tissue and the like (see for example U.S. Pat. Nos. 3,941,662, 3,102,082, and 4,142,940). Advantages that flexible, oxygen permeable containers may have are that they can provide a closed system, while the gas permeability of the container walls permits the use of conventional cell culture incubators without requiring the opening of the cell culture containers. Also, agitators and gas sparging may be eliminated by the use of such bags. The bags of course take up less storage and incubator space; will not break if dropped; and are disposable, eliminating the need to clean and resterilize glassware. Also, bags are generally cost effective disposable, which avoids the need to resterilize and depyrogenate reusable containers, as in the prior art.

U.S. Pat. No. 4,140,162 discloses special gas-permeable bags, these bags being in commercial use for the storage of platelets.

In accordance with this invention, various systems are provided to permit aseptic and even sterile filling of gas permeable bags with cell growth media, to facilitate cell culturing processes making use of such bags. There always is the serious need to preserve substantially aseptic conditions during cell culturing.

With this invention, the number of cell cultures which are lost due to a break in aseptic conditions may be reduced, while significant labor savings are provided as well.

DESCRIPTION OF THE INVENTION

In this invention, a system is provided for metering nutrient media to at least one cell culture container in substantially aseptic manner. The system comprises a media flow conduit which defines at one end means for substantially aseptic communication with a source of said media. Typically, a branch conduit extends from the flow conduit at a location spaced from its ends. The branch conduit communicates with means for receiving a predetermined-volume aliquot of media through the media flow conduit from said one end. Alternatively, other flow metering means may be provided.

The flow conduit defines a portion downstream from the branch conduit which is adapted to communicate with the cell culture container or containers. Each container is a flexible bag, at least part of which is made of a material providing at least 2 times the oxygen diffusion between the bag interior and exterior, when compared with an identically-sized, sealed bag having polyethylene walls 0.013 inch thick.

Thus, a large container of nutrient media may be connected to the system, and one or more aliquots of predetermined volumes of media may flow through the media flow conduit, with the aliquots being formed by an appropriate means. Thereafter, the individual aliquots may be sent to individual, flexible bags so that desired volumes of media may be inserted into any number of said flexible bags under aseptic conditions. Because the bags have adequate oxygen and carbon dioxide diffusion through their walls, they may be used for cell culturing while providing the advantages described above.

The large, nutrient media container may have gas and water-impermeable walls for stable storage of the media, contrary to the flexible bags used herein.

In one instance, the means for receiving the predetermined-volume aliquots may be a container or chamber such as a burette, or even a flexible, collapsible bag connected to the branch conduit, often with a 3-way valve being positioned at the junction of the media flow conduit and branch conduit to control flow into and out of the branch conduit. In another example, the branch conduit may connect with a syringe, the plunger of which may be used to draw the predetermined-volume aliquots, one after another, into the syringe. The flow conduit in this circumstance may define one-way valve means which are positioned upstream and downstream from the branch conduit, to permit only downstream flow as controlled by the syringe. Thus, one may draw a predetermined amount of media into the syringe by pulling the plunger out, and then expelling it back into the flow conduit. Because of the one-way valve system, that volume of fluid is forced downstream to provide a connected, flexible bag with a predetermined-volume aliquot of media.

The downstream portion of the flow conduit may define a plurality of branching conduit end portions, each end portion being connected in substantially aseptic manner to one of said flexible bags. The branching conduit end portions and bags may each define sterilizable connection means, permitting the establishment of sterile connection between said bags and branching conduit end portions without subjecting the whole system to sterilizing conditions. Such sterilizable connection means have been approved and used in the manufacture of medical sets by Travenol Laboratories, Inc. of Deerfield, Ill., and other known sterilizable systems exist as well. See in particular U.S. Pat. No. Re. 32,056.

Likewise, similar sterilizable connection means for forming a sterilized connection with the media source may be used to obtain aseptic connection at the upstream end of the system, without subjecting the whole system to sterilizing conditions.

Additionally, the flow conduit may carry an access site between the one end at its upstream end, and the branch conduit. For example, this access site may be used to add serum, when that is a desired component, of each aliquot of media liquid by first passing some of the aliquot of media liquid through the branch conduit; then adding some serum through the access site; and finally adding the final amount of media liquid to fill the predetermined aliquot, which is then passed once again through the branch conduit downstream to a flexible bag.

Additionally, the flexible bag of this invention may define an outer enclosing wall, and an inner, open cellular structure which is compatible with growing cells and serves as a site for cellular adherence. Preferably, the inner, open cellular structure is rather flexible, so that the bag may be provided in initial condition where it is wrapped in shrink wrap means under compressive pressure, causing the cellular structure within the bag to be in a relatively collapsed configuration, to cause the bag to be thinner than in its configuration of use. Accordingly, when the shrink wrap is removed, the bag and cellular structure can expand to assume their normal condition of use.

As a result of this, the flexible bags of this invention may have very high interior surface area, serving as adherence sites for cells that are cultured while adhering to a surface. The nature of the material of the cellular structure may be of any appropriate and compatible material for culturing cells. Preferably, the cellular structure may be of the honeycomb type with hexagonal channels passing through it. The hexagonal (or other shaped) honeycomb cell passage ways preferably are aligned to terminate adjacent the access port means in the bag. Likewise plastic open cell foams, fibrous materials including hollow fibers, or any other open-cell type materials may be used as the cellular structure to provide adherence areas to cells that adhere to a surface during culturing.

In addition to the open cellular structure, other means may be provided inside the flexible bag to increase the area of cell adherence. For example, a microcarrier such as small glass spheres or sodium alginate may be employed to increase surface area for cell adherence.

Alternatively, bags with open, empty interiors may be used for culturing cells which do not adhere to surfaces, for example, suspension cells such as most hybridoma cells and human monocytes, in a bag made of a nonadherent material.

The other parts of the system of this invention may be made of conventional plastic materials for such products as is currently available. The tubular conduit members may be made of a conventional polyvinyl chloride formulation, but preferably, the flexible bag may be made of an oxygen and carbon dioxide permeable material of a formulation as described in U.S. Pat. No. 4,140,162. Additionally, thin-walled polyethylene, or polytetrafluoroethylene, may be used for such bags, as described in the prior art. Other formulations as well may be used for gas-permeable bag walls, for example poly(ethylene-vinyl acetate), silicones, or a hydrocarbon resin sold under the trademark TPX.

DESCRIPTION OF THE DRAWINGS

In the drawings,

FIG. 1 is an elevational view of a system for metering nutrient media to a cell culture container in substantially aseptic manner.

FIG. 1A is a detailed perspective view of the connectors used for connecting the media flow conduit with a flexible bag in accordance with this invention.

FIG. 2 is an elevational view of an alternative embodiment of media flow conduit.

FIG. 3 is an elevational view of an alternative embodiment of media flow conduit which may be used in conjunction with the media storage bag and the cell culture container of FIG. 1, to provide liquid media to said cell culture container.

FIG. 6 is an elevational view of another embodiment of cell culture container in accordance with this invention.

FIG. 7 is an elevational view of the bag of FIG. 6, rotated 90 degrees about its longitudinal axis, with portions broken away, and showing how it may be packaged in a shrink wrap package.

FIG. 8 is a fragmentary, longitudinal sectional view taken along line 8—8 of FIG. 7.

FIG. 9 is an elevational view, with portions broken away, of the bag of FIG. 6 after the shrink wrap has been removed.

FIG. 10 is a sectional view taken along line 10—10 of FIG. 9, showing the expanded, honeycomb nature of the cellular structure within the bag.

DESCRIPTION OF SPECIFIC EMBODIMENTS

Figure 4:
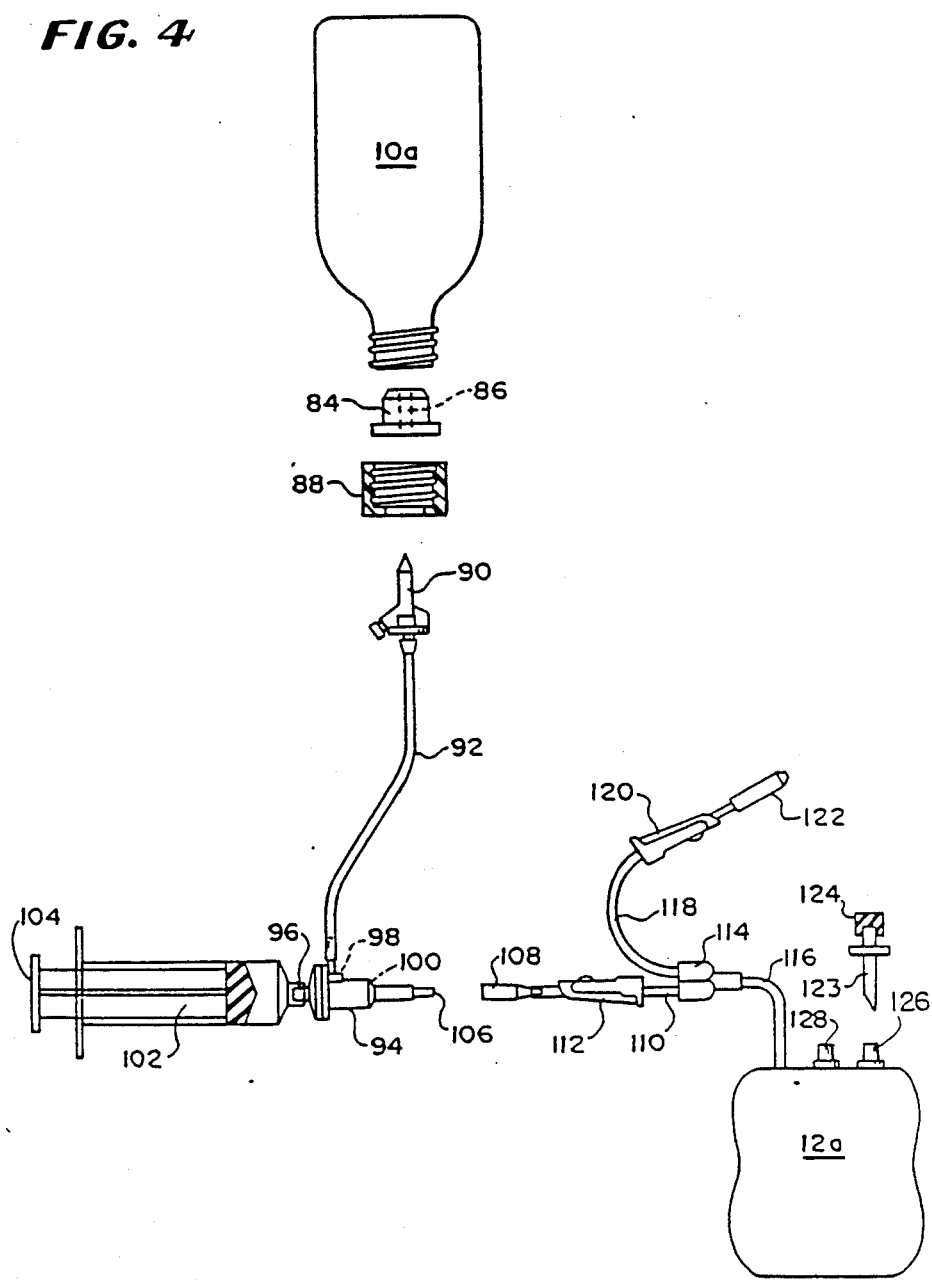
FIG. 4 is an elevational view of another alternative embodiment of media flow conduit which may be used in conjunction with a media storage bottle and the cell culture container of FIG. 1, to provide liquid media to said cell culture container.

Referring to FIGS. 1 and 1a, a first embodiment of this invention is disclosed. A source of media 10 is disclosed as a flexible bag of nutrient media for the growth of a certain cell. The cells may be hybridomas from which monoclonal antibodies may be obtained by culturing.

Alternatively, the cells may be white blood cells such as lymphocytes from a cancer patient. In this circumstance, as is taught in the literature, culturing of the lymphocyte with a lymphokine such as interleukin-2 can provide an activated lymphocyte which is more active in the process of identifying and killing tumor cells. These activated lymphocytes may then be returned to the patient for treatment of the cancer.

In accordance with this invention, individual bags 12 for the culturing of cells are filled in a substantially aseptic manner with at least one predetermined-volume aliquot of media through a media flow conduit 14.

Thereafter, the cells for culturing are placed into bag 12. The specific media used will be any appropriate type of media desired, depending on the particular cells to be cultured. Many different varieties of media are taught in the prior art. It should also be known that the verb "culture" may refer to the maintenance of cells and their multiplication by growth, but alternatively, it can apply to situations where the cells do not multiply but simply are treated (for example, with a lymphokine) to change their characteristics. One cell medium that may be used for lymphocytes is a medium consisting of RPMI 1640 (low endotoxin; M.A. Bioproducts of Walkersville, Md.) also including 10 units per ml of penicillin, 10 micrograms/ml. of streptomycin sulfate, 2 ml. of glutamine, 5 micrograms per ml. of gentamicin, and 2 percent by weight of heat-inactivated human AB serum. This formulation is taught in Rosenberg U.S. patent application Ser. No. 763,657, filed Aug. 8, 1985, now U.S. Pat. No. 4,690,915. Appropriate media for hybridoma cells are widely available in the literature.

Media flow conduit 14 defines at one end 16 a conventional spike for penetration of media bag 10. If a media bottle is used with a conventional plug in its mouth of a design used with parenteral solution bottles, spike 16 may be a conventional vented spike of known design.

Media flow conduit 14 carries a conventional injection site 18 into which supplemental materials may be inserted by a needle syringe in a generally aseptic manner, for example, serum such as fetal bovine serum, amino acids, vitamins, or antiobiotics, which typically are not stored with the artificial nutrient media within bag 10.

Media flow conduit 14 comprises flexible tubing typically of polyvinylchloride or any other conventional tubing of the type used in parenteral solution administration and the like. Roller clamp 20 may be provided to control flow through the tubing, and may be of conventional design.

Media flow conduit 14 may have a dividable connection comprising a pair of luer lock connectors 22,24 which are connected together with an aseptic seal, being initially provided in sterile condition as long as protective caps 26, 28 have not been previously removed. Designs of Luer connectors are known to the art, some of them being disclosed in Dennehey et al., U.S. Pat. No. 4,346,703 and Ruschke et al U.S. Pat. No. 4,452,473.

Liquid nutrient media may flow from bag 10, through the connection of members 22, 24 into 3-way valve 30, which is also of conventional design, being commercially sold on various parenteral solution sets and the like by various companies. The rotatable handle 32 of valve 30 may be in a position so that the flow travels upwardly through branch conduit 34, which may connect through a burette 36, carrying a vent 38 and an injection site 40. Such burettes are also in commercial use in the parenteral solution field. One such burette is described in U.S. Pat. No. 4,322,247. This particular burette may be connected to branch conduit 34 by the action of connectors 42, 44 of design similar to connectors 22, 24.

Accordingly, a predetermined-volume aliquot of nutrient media from bag 10 may flow through media flow conduit 14 into burette 36, which has volume measuring indices, until the predetermined volume of the aliquot has been reached. Then, the user can shift 3-way valve 32 to cause the flow to return from burette 36, through branch conduit 34, into the portion 14a of conduit 14 which is downstream from branch conduit 34. Clamp 46, of conventional design, may be loosened to permit such flow. Downstream portion 14a may be connected to 3-way valve 30 by more connectors 48, 50 of similar design to connectors 22, 24.

In those circumstances where the predetermined-volume aliquot is of a constant volume every time, burette 36 may be replaced with a simple, collapsible bag having a filled volume which corresponds to the desired volume of the aliquot. The burette is useful when variable volume aliquots are intended to be drawn from media container 10 into cell culture bag 12.

A pressure head may be provided to the system by raising media bag 10 about branch conduit 34, the volume metering means 36 such as the burette being raised over bag 12 as well.

Connection to bag 12 by conduit 14a may be obtained by the use of similar connectors 52, 54 for placing the predetermined-volume aliquot of nutrient media into bag 12. Bag 12 per se is known to the art, being described in U.S. Pat. Nos. Re. 31,135 and 4,140,162. The particular material of bag 12 has a high capability for oxygen and carbon dioxide diffusion, very substantially over that of polyvinylchloride and other materials in prior art bags. Also, fewer leachable materials are present in the bag materials of the cited U.S. Pat. No. 4,148,162.

Typically, bag 12 is filled with nutrient media and cells to no more than about one quarter to one half of its full capacity, to provide a relatively high ratio of internal surface area of volume of the media and cells, so that abundant oxygen can diffuse into the bag and carbon dioxide can diffuse out of the bag, to facilitate cell metabolism and growth.

Thus, by the system of this invention, one or more cell culture bags 12 can be prepared for receiving their cells for culturing by receiving one or more aliquots of nutrient media of predetermined volume, under substantially aseptic conditions to minimize the current problem commonly encountered in cell culturing today of contamination of many of the cell culture samples.

The cells themselves may be inserted into bags 12 by removal of conventionally designed plastic port protectors 56 which close access port 58. The cells may be added through tubular sampling site coupler 60, which penetrates an internal diaphragm in port 58 to gain access to the container. Coupler 60 may have a conventional injection site 61 on its outer end. If desired, coupler 60 may remain within port 58 to close it during the culturing operation. Alternatively, an added closure may be provided for port 58. If desired, a needle syringe may be used to pierce injection site 61 to inject the cells into bag 12. Otherwise, bag 12 may carry its own injection site.

To separate bag 12 from its media flow conduit set 14, 14a, one may place a heat seal or other seal across a portion of the tubing 14a, which may be made of polyvinylchloride, or another thermoplastic material. Alternatively, short length of tubing 62 may be transversely sealed. One then cuts through the seal while maintaining its integrity on preferably both sides so that bag 12, with its aliquot of nutrient media, can be separated and taken for use in a cell culture.

Turning to FIG. 2, a simplified media flow conduit 64 is provided, being the length of flexible tubing 66 which is shown to serve as roller pump tubing in a conventional roller pump 68, which is only partially and schematically shown, and connector 67 of conduit 64 may be a connector of conventional design, similar for example, to connector 22. End 68a provides a connector which may be similar to connector 24.

Conduit 64 serves as a substitute for branch conduit 34, 3-way valve 30, and burette 36. It may be connected by connectors 67, 68a to media flow conduit portions 14, 14a to provide an assembly that is otherwise substantially equivalent to that shown in FIG. 1, where the individual aliquots of nutrient media flow in their predetermined volumes in a manner as governed by roller pump 68.

Turning to FIG. 3, another embodiment is disclosed, serving as a substitute for branch conduit 34, 3-way valve 30, and burette 36. A differing branch conduit 63 is provided in a set portion 65 which carries connectors 67a, on their respective ends for connecting with other portions 14, 14a of the media flow conduit. Clamp 70 may also be provided as shown.

Adjacent branch conduit housing 72 lie a pair of one way valves 74, 76 of conventional design to assure that flow through conduit 65 goes only in one direction from connector 67a to connector 69. Connector 67a may connect with media flow conduit portion 14, while connector 69 connects with portion 14a. A syringe 78, of conventional design, may be connected by a simple luer connection to branch conduit 63 (removing respective end caps 80, 82). Syringe 78 carries volume indicating indicia.

Accordingly, when the entire set is set up, with the structure of FIG. 3 replacing one-way valve 30, branch conduit 34, and burette 36, one can simply use syringe 78 as a pump to draw from container the predetermined-volume aliquot, and then to force it downstream to conduit portion 14a and bag or bags 12, due to the action of one way valves 74, 76. Many designs of appropriate one way valve are known such as duckbill valves, flapper valves and the like. One particular one way valve that may be used for valves 74, 76 is a valve sold by Travenol Laboratories, Inc. as part of a parenteral solution set.

Referring to FIG. 4, another system in accordance with the system is provided for transferring liquid nutrient media from a rigid media bottle 10a to a culture container 12a, which may be a flexible bag made in accordance with conventional technology.

Stopper 84 fits in the neck of bottle 10a, and defines a port 86 for spike penetration. Threaded cap 88 is fitted onto the neck of bottle 10a to retain stopper 84 in position.

Integral airway spike 90, of a commercial design for penetration of bottles of parenteral solution is provided, being connected to a first length 92 of a media flow conduit. Conduit 92 terminates in molded assembly 94, which includes branch conduit 96 and a pair of one-way valves 98, 100 respectively positioned upstream and downstream from branch conduit 96. A more compact design of valves for the same purpose combined into a single structure is disclosed in U.S. Pat. No. 4,084,606.

Syringe 102, of conventional design, may connect to branch conduit 96 so that as the syringe is pumped, media solution flows downstream in predetermined-volume aliquots as controlled by each stroke of the syringe handle 104.

Assembly 94 also carries male luer connector 106, which is adapted to connect with female luer 108, which, in turn, is carried by media flow conduit section 110. Conduit section 110, in turn, is controlled by a roller clamp 112, and communicates through Y-connector 114 and conduit section 116 to culture container 12a. Container 12a may be a collapsible bag made in accordance with U.S. Pat. No. 4,140,162 or any other flexible sheeting material having the required high oxygen and carbon dioxide diffusion, when compared with a bag having walls of polyethylene.

The remaining branch tube 118 is controlled by another roller clamp 120, and may terminate in a male needle adapter 122 or another conventional connector.

In use, sampling site coupler 123 may be a hollow tube with a pointed end plus a needle-piercable situs 124, and may be used to penetrate access port 126 of container 12a to insert the cells for culturing, typically after filling of container 12a with the predetermined-volume aliquot of media solution via syringe 102. After such filling, in a manner previously described, roller clamp 112 may be closed and connectors 106, 108 separated to remove the container to its culturing environment, or tube 110 may be heat sealed shut. Added nutrients or other agents may be added through access port 128 as desired. Situs 124 may be repeatedly pierced as desired for adding or removing media or other agents.

After the culturing phase, further processing steps may be performed. In the case of suspended cells where protein production is an end goal, the product-rich supernatent may be separated from the cells and harvested, such as with a centrifugation or membrane system. Alternatively, the contents of the culture container may be transferred to other containers for further processing through tubings 116, 118 and adapter 122.

Figure 5:
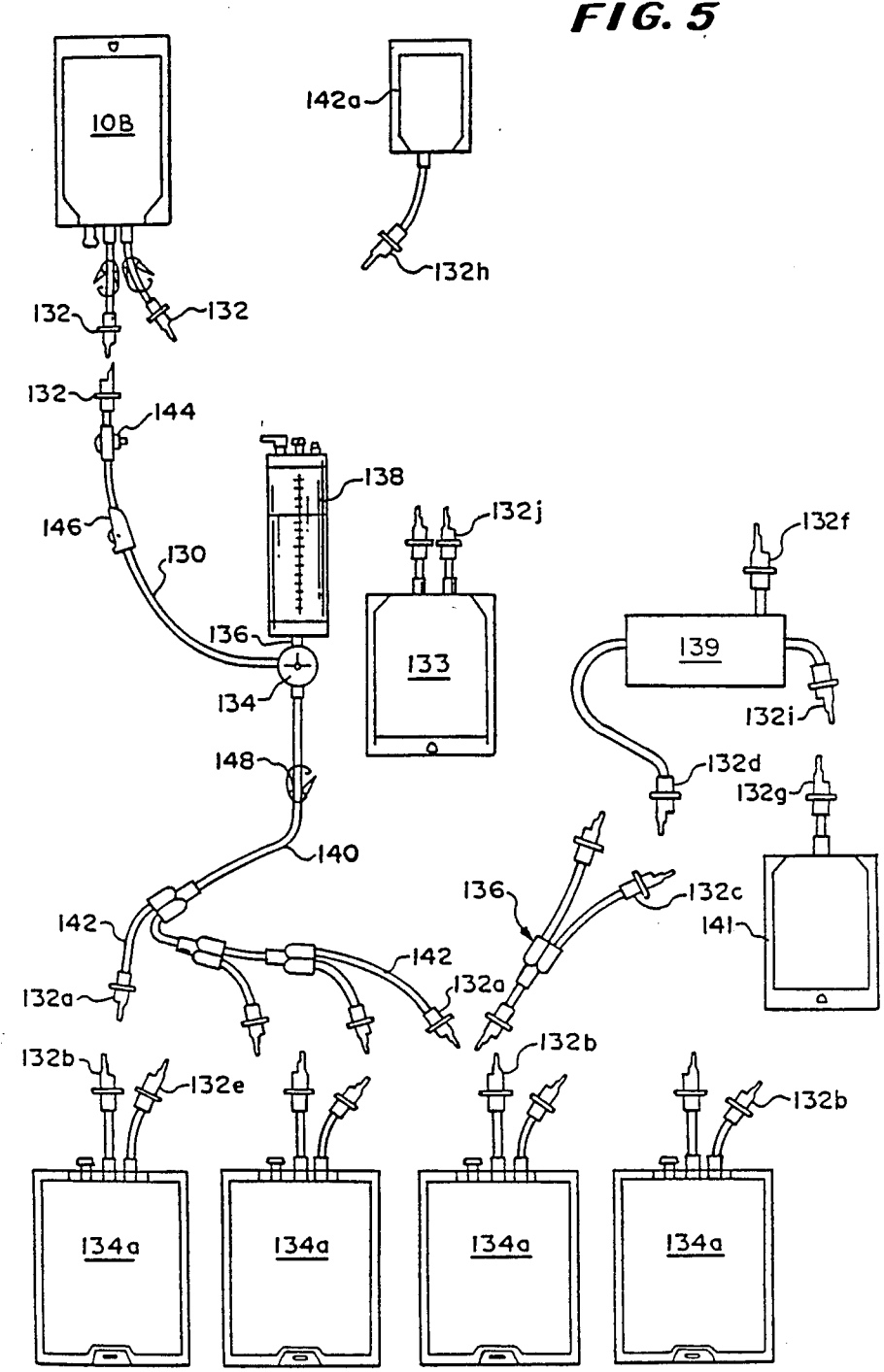
FIG. 5 is an exploded view of another system in accordance with this invention for transferring in sterile manner media from a supply container to a plurality of flexible cell culture containers, including ancillary equipment that may be used in conjunction therewith.

FIG. 5 is an exploded view of another system in accordance with this invention in which sterility of the materials processed may be assured with a higher degree of reliability. Nutrient media container 10b, of a design similar to either previous embodiment, may be connected to a media flow conduit 130 by means of a pair of identical sterile connector devices 132, a specific embodiment of which has been demonstrated as a product by Travenol Laboratories, Inc. and which operate in accordance with the principles described in U.S. Pat. No. Re. 32,056. These connectors are locked together, and then irradiated with intense light of infrared radiation, resulting in a sterile, fluid pathway being formed between the two connectors 132.

As in an earlier embodiment, three-way valve 134 is provided, carrying branch conduit 136 which connects with a burette 138. Alternatively, burette 138 may be replaced with a small, connect bag if desired for cost savings with the maximum fluid volume of the bag being indentical to the desired, predetermined-volume aliquot.

Downstream portion 140 of the flow conduit is branched as shown to provide a series of branches 142, each of which is terminated with a sterile connector 132a, may be connected in sterile manner with a sterile connector 132b of one of the series of flexible bags 134a. In this circumstance, by appropriate clamping of lines 142 (which may be equipped with slide clamps or the like), the desired predetermined-volume aliquots of media solution may be metered from container 10b, through branch conduit 136 and burette 138, sequentially into each of bags 134 after the sterile connection between connectors 132a and 132b has been made.

If desired, added connection sites may be provided by Y-connector 136 which includes a Y-shaped arrangement of conduits, each terminated with a sterile connector 132c, similar in design to sterile connectors 132a. By the use of members 136, the number of available sites for connection with bags 134a may be increased by any desired number.

Added ancillary equipment 139 constitutes a y-connector having a filter. Sterile connectors 132d may be connected into line with connectors 132a or 132c, for example, so that the media material may be filtered. Alternatively, after culturing of the cells has taken place in bag 134a, the contents of the bag may be connected in sterile manner to connector 132d through its second connector 132e, and the contents of the bag filtered. The filtrate then can pass through another connector 132f another container such as filtrate container 133 with connectors 132j, for storage or further processing. By this manner, filtrate, which may carry a biochemical product manufactured by the cells, may be separated from the cells in reliably sterile manner, once all the components have been initially sterilized.

Receptacle container 141 may also be used in any desired manner with its connector 132g, for example to connect its connector 132g with with the remaining outlet connector 132i of filter member 139.

As may be desired, serum may be added to the media by means of serum container 142a, carrying its sterile connector 132h. It may be used to make connection with the second connector 132 of media bag 10b so that the serum and media may be mixed prior to the metering of the various aliquots into the respective bags 134a. Alternatively, connector 132h may be connected through the use of ancillary device 139.

Other parts of the set such as injection site 144 and clamps 146, 148 may be provided as deemed appropriate.

Turning now to FIGS. 6-10, a specific type of flexible bag 150 is disclosed for use in this invention, being analagous in function and outer structure to bags 12, 12a, and 134a. Bag 150 may be made of flexible, plastic sheeting having the desired high oxygen and carbon dioxide diffusion characteristics as discussed above. However, bag 150 is provided with a facility for culturing cells that need to adhere to a surface. By this invention, a bag having an ultrahigh surface area in its interior is provided so that a large number of such cells may be cultured in the bag under conditions that are optimal for their growth and development.

As shown, flexible bag 150 may be made of a film wall material having the desired, adequate oxygen and carbon dioxide diffusion capability to permit the culturing of cells therein under sealed, substantially aseptic conditions. Bag 150 defines an outer enclosing wall 152 which may, for example, be the remainder of a blow molded parison in accordance with blow molding technology, or may be made of a pair of peripherally sealed sheets in accordance with heat or R.F. sealing technologies. Within bag 150 is an inner, open cellular structure which is capable of supporting growing cells, and serves as a site for cell adherence. See particularly FIGS. 9 and 10 for broken away and sectional views of the cellular structure 154. An enlarged view of the hexagonal cells 156 is shown in FIG. 10. Each cell 156 is of hexagonal cross section, and is typically open at its respective ends, rather in the form of a honeycomb shape, with the individual cells 154 being aligned with one end of each honeycomb cell passageway 158 terminating adjacent the access ports 160 of said bag.

The open cellular structure may be made of any desired material suitable for the adhesion and healthy maintenance of the cells, particularly relatively high surface energy polymers, preferably having a surface energy of at least about that of cellulose for example. Examples of such materials include cellulose, polyester materials, high surface energy nylon (such as that sold by the Hexcel Co. of California), corona discharge treated polyolefin or the like.

The open cellular material may, in the alternative, comprise hollow fibers, particularly those extending in a manner analagous to the direction of extension of open cells 158. The material may be an open-celled foam, or a fibrous mass, either woven or nonwoven. The term "cellular" is intended to imply open porosity, not necessarily indicating that discreet cells are present as in an open-celled foam, although such is intended to be included as one possible type of open-celled material.

The flexible bag 150 may be compressed in packaging by wrapping in a known heat-shrink wrap. The advantage of packaging bag 150 by a shrink wrap technique as shown in FIGS. 7 and 8 is primarily to save space until bag 150 is ready for use.

Sterile filter vent 164 may be provided for communication between the interior and exterior of the bag to facilitate this process. Specifically, the vent may contain a filter of hydrophobic material in accordance with known technology which exhibits strong bacteria blocking characteristics.

As shown in FIG. 8, cellular structure 156 may be compressed by the compressive action of the heat shrink wrap 162, for efficient shipping and storage.

When it is desired to make use of bag 150, shrink wrap 162 may be torn away, permitting bag 150 to expand by natural expansive action of open cellular material 154, to the configuration shown in FIGS. 9 and 10. Alternatively, this expansion may take place upon softening of cellular material 154 as it is wetted with liquid nutrient media.

During the culturing of cells in a bag similar to bag 150, it may be desired to provide a mechanical means to gently knead the bag to assure circulation of nutrient media through the open cells of material 154, so that oxygen and carbon dioxide may diffuse into and out of bag wall 152, and no stagnant pockets of nutrient media will form, which may interfere with cell viability.

The above has been offered for illustrative purposes only, and is not intended to limit the scope of the invention of this application, which is as defined in the claims below.

That which is claimed is:

1. A method for metering nutrient media into a plurality of cell culture containers in substantially aseptic manner, which method comprises passing liquid nutrient media through a media flow conduit which is in substantially aseptic connection at one end with means providing a source of said media; passing said media from the flow conduit through a branch conduit extending from said flow conduit at a location spaced from its ends, into means for receiving a predetermined-volume aliquot or media; passing said predetermined-volume aliquot of nutrient media again through the branch conduit into and through a downstream portion of said media flow conduit, said downstream portion defining a plurality of branching conduit end portions, said end portions being attached in substantially aseptic manner each to a flat, flexible cell culture container; and sequentially filling said cell culture containers each with a predetermined-volume aliquot of media from said receiving means; at least part of said containers being made of a material capable of providing at least 2 times the oxygen diffusion and at least 2 times the carbon dioxide diffusion between the bag interior and exterior, compared with an identically-sized, sealed bag having polyethylene walls 0.013 inch thick.

2. The method of claim 1 which further includes passing a portion of said predetermined-volume aliquot of media through the media flow conduit, then adding to the media flow conduit a predetermined amount of serum, followed by adding more liquid media through said media flow conduit, to fill said receiving means with a predetermined-volume aliquot comprising a mixture of liquid media and serum, said aliquot being then transferred to said flexible, flat-collapsible bag.

3. The method of claim 1 including the step of forming a sterile connection between the media flow conduit and a source of nutrient media without subjecting the whole system to sterilizing conditions.

4. The method of claim 1 including the step of connecting ends of said branch conduit with said separate, flexible bags under conditions to form substantially sterile connections without subjecting the whole system to sterilizing conditions.

5. A method for metering nutrient media into a plurality of cell culture bags in substantially aseptic manner, which method comprises passing liquid nutrient media through a media flow conduit which is in substantially aseptic connection at one end with a source of said media, and metering aliquots of said media through a downstream portion of said media flow conduit through a plurality of branching conduit end portions, into a plurality of flat, flexible bags which are separately attached to individual conduit end portions in substantially aseptic manner, and sequentially filling said flat bags with a predetermined-volume aliquot of media, at least part of which bags are made of a material capable of providing at least two times the oxygen diffusion and at least two times the carbon dioxide diffusion between the bag interior and exterior, compared with an identically sized, sealed bag having a polyethylene wall 0.013 inch thick, including the step of sequentially and repeatedly passing aliquots of predetermined volume through said downstream, branched portion of said flow conduit sequentially into each of said plurality of flexible bags, whereby said plurality of bags may be filled with said predetermined-volume aliquots of media in substantially aseptic manner, and culturing human white blood cells in the nutrient media within said flexible bags.

6. The method of claim 5 which further includes passing a portion of said aliquot of media through the media flow conduit, then adding to the media flow conduit a predetermined amount of serum followed by adding more liquid media through said media flow conduit and to said flexible bag, whereby said predetermined-volume aliquot of media, containing serum, is provided to said bag.

7. The method of claim 5 including the step of forming a sterile connection between the media flow conduit and a source of nutrient media without subjecting the whole system to sterilizing conditions.

8. The method of claim 7 including the step of connecting the conduit end opposed to said one end with at least one of said flexible bags under conditions to form substantially sterile connections without subjecting the whole system to sterilizing conditions.

* * * * *